(12) United States Patent
Miller (10) Patent No.: US 6,435,004 B1
(45) Date of Patent: Aug. 20, 2002

(54) APPARATUS AND PROCESS FOR AEROSOL SIZE MEASUREMENT AT VARYING GAS FLOW RATES

(76) Inventor: Nicholas C. Miller, 12746 Ethan Ave. N., White Bear Lake, MN (US) 55110

( * ) Notice: Subject to any disclaimer, the term of this patent is extended or adjusted under 35 U.S.C. 154(b) by 0 days.

(21) Appl. No.: 09/152,164

(22) Filed: Sep. 11, 1998

Related U.S. Application Data (60) Provisional application No. 60/058,682, filed on Sep. 12, 1997.

(51) Int. Cl.$^7$ .................. G01N 33/497; G01N 15/02
(52) U.S. Cl. .................. 73/23.3; 73/23.2; 73/28.01; 73/863.03; 73/865.5
(58) Field of Search .................. 73/23.3, 863.02, 73/23.2, 863.03, 865.5, 28.01, 28.04, 28.05, 28.06

(56) References Cited

U.S. PATENT DOCUMENTS

| | | |
|---|---|---|
| 3,478,600 A | 11/1969 | Lynn |
| 3,498,294 A * | 3/1970 | Zeff et al. ............. 73/23.3 X |
| 3,501,899 A | 3/1970 | Allen .................... 55/210 |
| 3,518,815 A | 7/1970 | McFarland et al. ........ 55/241 |
| 3,528,279 A | 9/1970 | Lasseur et al. .......... 55/22 X |
| 3,581,473 A | 6/1971 | Ririe, Jr. et al. ......... 55/219 |
| 3,741,001 A | 6/1973 | Fletcher et al. |
| 3,774,442 A | 11/1973 | Gustavsson |
| 3,791,196 A | 2/1974 | Lepper, Jr. |
| 4,527,435 A | 7/1985 | Hall et al. .............. 73/863.03 |
| 4,684,251 A | 8/1987 | Brouwer et al. ........... 356/315 |
| 4,902,318 A | 2/1990 | Stevens et al. ............ 55/270 |
| 5,052,425 A | 10/1991 | Hohenberg et al. ............ 137/1 |
| 5,090,258 A | 2/1992 | Yamasaki et al. ........ 73/863.03 |
| 5,109,708 A | 5/1992 | Lawless .................... 73/863.11 |
| 5,237,881 A | 8/1993 | Ross .................... 73/863.12 |
| 5,277,074 A * | 1/1994 | Poole et al. ........... 73/28.01 X |
| 5,302,191 A | 4/1994 | Koutrakis et al. ............ 95/285 |
| 5,332,512 A | 7/1994 | Wells .................... 210/790 |
| 5,343,767 A | 9/1994 | Marple et al. ........... 73/863.22 |
| 5,473,951 A | 12/1995 | Tomlin .................... 73/863.83 |
| 5,537,879 A | 7/1996 | Malczewski et al. .... 73/863.61 |
| 6,003,389 A * | 12/1999 | Flagan et al. ............. 73/865.5 |

FOREIGN PATENT DOCUMENTS

| | | | | |
|---|---|---|---|---|
| DE | 297 902 A7 | * | 1/1992 | ............. 73/28.01 |
| EP | 416 976 A1 | * | 3/1991 | ............. 73/28.01 |
| SU | 1226172 A | * | 4/1986 | ............. 73/28.01 |
| SU | 1328729 A1 | * | 8/1987 | ............. 73/28.01 |

* cited by examiner

Primary Examiner—Thomas P. Noland
(74) Attorney, Agent, or Firm—Faegre & Benson LLP (57) ABSTRACT

A measuring system and process for measuring the size distribution of particles in an aerosol with a time-varying flow utilizing a measuring instrument that utilizes a time-invariant flow rate is provided. The process includes employing a vacuum source to establish a constant flow through the measuring instrument. The vacuum generated by the vacuum source is used to draw an aerosol stream through an inlet incorporating a second stream of relatively particle free gas. The first and/or the second stream may be adjusted so that at any instant of time, the sum of the two streams is a constant value equal to the flow rate through the measuring instrument.

26 Claims, 5 Drawing Sheets

APPARATUS AND PROCESS FOR AEROSOL SIZE MEASUREMENT AT VARYING GAS FLOW RATES

CROSS-REFERENCE TO RELATED APPLICATION

This application is a completion application of U.S. Provisional Application Ser. No. 60/058,682 filed Sep. 12, 1997 and claims priority therefrom. U.S. Provisional Application Ser. No. 60/058,682 is incorporated by reference herein.

TECHNICAL FIELD

The present invention relates to an apparatus and process for the measurement of the size distribution of particles in aerosols. More particularly, the present invention relates to an apparatus and process that overcome the measurement limitations of instruments used to measure the size distribution of particles in aerosols, due to the instrument requirements for constant flow rate.

BACKGROUND OF THE INVENTION

Pharmaceutical aerosol delivery devices are often used to generate aerosols for the delivery of drugs to the respiratory tract. Generally, pharmaceutical aerosol delivery devices are of two types; self-propelled, and breath-propelled. Self-propelled aerosol delivery devices, exemplified by most pressurized Metered Dose Inhalers, generate an aerosol cloud by using energy supplied by the delivery device itself, i.e., liquefied gas propellants, battery operated fans, or compressed air. In contrast, breath-propelled aerosol delivery devices depend on externally-supplied negative pressure to generate the aerosol, such as the negative pressure created by the act of inhaling. For both of these types of delivery devices, the size distribution of the particles in the generated aerosol in the airway and lungs depends on the characteristics of the air stream into which the aerosol is dispensed. In addition, the efficiency of the delivery of these types of devices depends on the flow rate of gas which is drawn through the device.

In general, methods for measuring the size distribution of aerosol particles require that the aerosol particles are within a well-defined gas flow field. For example, inertial classifiers, one type of such instruments, operate by suspending aerosol particles in a moving gas stream. The stream is then caused to change directions, which in turn, causes the aerosol particles to cross the flow streamlines. In this manner, the aerosol particles are removed from the gas stream. In order for these types of instruments to operate properly, the flow rate of the gas stream must be constant.

The cascade impactor, which is a type of inertial classifier, is especially well-suited to the measurement of the size of aerosol particles. For example, U.S. Pat. No. 5,343,767 describes one example of a particular kind of a cascade impactor. Generally, cascade impactors comprise a plurality of collection stages arranged in series, with each stage designed to collect particles of successively smaller sizes. Within each stage, the gas stream is caused to flow through one or more nozzles to give the stream a relatively high velocity. The nozzles are directed perpendicular to a flat collection surface that is relatively close (less than about ten times the nozzle diameter) to the nozzle outlet. Depending primarily upon the speed of the gas stream through the nozzle, particles greater than a certain size strike the collection surface where they are retained for subsequent quantitation in a separate step. Successive stages have either fewer nozzles or smaller nozzles, so that the gas stream undergoes higher speeds and hence deposits smaller particles on the collection surface. The total gas flow rate through the cascade impactor must remain at a known and constant value during the course of a measurement because the size of particles deposited on a particular stage depends largely on the speed of gas flow.

However, both types of aerosol delivery devices are intended ultimately to produce aerosols into the varying flow rates which characterize the human breathing cycle. The size measurement of the particles in an aerosol in an air flow stream which is representative of the end-use situation thus presents a challenge. That is, although most measurement devices require constant gas flow, both types of delivery devices (i.e., self-propelled and breath propelled), are ultimately used in a situation with a variable flow rate. Thus, the requirement of constant flow through a measurement instrument cannot be satisfied when measuring the particle size distribution generated by a device operated in a variable flow rate. Thus, prior art methods for measuring the particle size distribution of aerosols are inadequate, in that the flow rate through the delivery device is maintained at a constant flow rate which is not representative of the end-use situation.

Generally, prior art apparatus' for the measurement of the size distribution of particles in an aerosol consist of a measuring instrument, such as an inertial classifier, coupled to an aerosol generating device, such as the inhaler devices described hereinabove. A vacuum source is coupled to the measuring instrument and is utilized to generate a relatively constant gas flow through the measuring instrument. Because the measuring instrument is coupled to the aerosol generating device this relatively constant gas flow must also pass through the aerosol generating device. Inasmuch as the measuring instrument is intended to measure the size distribution of the particles in an aerosol as distributed during a breathing pattern, this is an undesirable result. That is, it would be preferable if the flow from the aerosol generating device were comparable to the flow and pattern of a breathing cycle. More preferably, the flow through the aerosol generating device would be adjustable so as to correspond to different breathing flow rates, i.e., as for a child as opposed to an adult.

Thus, there is a need for an improved system for the measurement of the particle size distribution in an aerosol that includes an instrument utilizing a constant gas flow rate, yet capable of measuring an aerosol of varying flow rate.

SUMMARY OF THE INVENTION

The aforementioned shortcomings and disadvantages of the prior art are overcome by the apparatus and process provided by the present invention. Specifically, the present invention relates to an apparatus and process for measuring the size distribution of particles in an aerosol stream utilizing a measuring instrument that utilizes a generally constant gas flow rate.

Specifically, the apparatus of the present invention is a measuring system comprising a measuring instrument capable of measuring the size distribution of particles in an aerosol. Preferably, the measuring instrument will be one generally utilizing a constant gas flow rate. The measuring system further comprises a vacuum source, sealably coupled to the measuring instrument, that is utilized to force a constant flow rate of gas through the measuring instrument. Also provided is an inlet tube sealably coupled to the measuring instrument at a first end and an aerosol generating device connected to the inlet tube at a second end.

It is preferred that the connection between the inlet tube and the aerosol generating device is gas tight. That is, it is preferred that the connection between the inlet tube and the aerosol generating device is sufficiently leak-free that essentially all of the gas which enters the inlet tube is drawn in through the aerosol generating device. In this manner, the inlet tube functions to receive a first flow of a gas, as well as an amount of an aerosol generated by the aerosol generating device.

It is further preferred that the measuring system of the present invention comprises a mixing chamber that functions to couple the inlet tube to the measuring instrument. Preferably the mixing chamber comprises an inlet, hereinafter referred to as the mixing chamber inlet, capable of receiving a second flow of gas. In operation of the measuring system of the present invention, the first flow and/or the second flow of gas are preferably adjustable so that the combination of the first flow and the second flow are equal to the constant flow rate generated by the vacuum source.

Also provided by the present invention is an improved process for the measurement of the size distribution of particles in an aerosol stream. The process comprises employing a vacuum source to establish a constant flow through a measuring instrument. The vacuum generated by the vacuum source is used to draw an aerosol stream through an inlet incorporating a second stream of a gas. Preferably, the second flow of a gas is relatively particle free gas. The first flow and/or the second flow are adjustable so that at any instant of time, the sum of the two streams is a value equal to the constant flow rate through the measuring instrument.

BRIEF DESCRIPTION OF THE DRAWINGS

The above mentioned and other advantages of the present invention, and the manner of attaining them, will become more apparent and the invention itself will be better understood by reference to the following description of the embodiments of the invention taken in conjunction with the accompanying drawings wherein.

DETAILED DESCRIPTION OF THE PREFERRED EMBODIMENTS

As used herein, the term "aerosol" is meant to indicate a suspension of fine solid or liquid particles in gas. Thus, the measuring system and process of the present invention may be used to measure the particle size of atomized particles of liquid as well as being useful to measure the particle size of atomized particles of solids.

Figure 1:
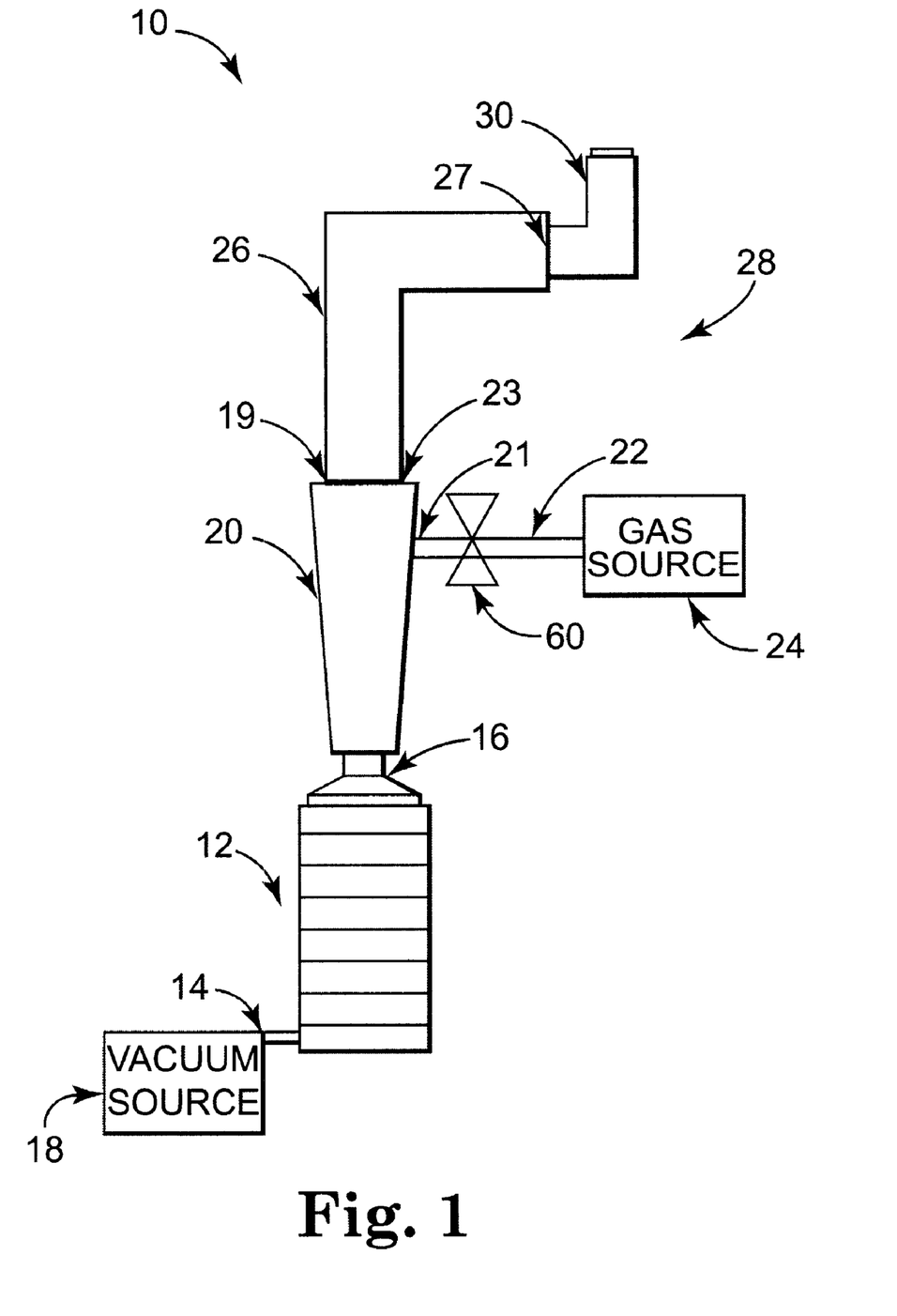
FIG. 1 is a schematic side view of one embodiment of the improved apparatus in accordance with the present invention.

FIG. 1 is a schematic side view of one embodiment of improved aerosol measuring system 10, in accordance with the present invention. Aerosol measuring system 10 includes a measuring instrument 12 and a gas regulating and aerosol conduit assembly 28 for coupling an aerosol generating device 30 to the measuring instrument 12. Measuring instrument 12 can be a commercially available or otherwise conventional cascade impactor, and has a vacuum port 14 and an aerosol receiving inlet port 16. Measuring instruments 12 of the type described above are commercially available from Graesby Corp., Smyrna, Ga. or MSP Corp, Minneapolis, Minn., and are described in USP publication *Pharmaceutical Forum*, 22, 3084 (1996). A vacuum source 18 is connected to vacuum port 14 to generate a flow of air or other gas into measuring instrument 12 through aerosol receiving inlet port 16. Typically, vacuum source 18 is adjusted to generate a gas flow of a predetermined rate into measuring instrument 12.

Gas regulating and aerosol conduit assembly 28 includes a mixing chamber 20, inlet tube 26 and valve 60. Valve 60 is positioned on mixing chamber inlet 22 and is actuated to regulate the flow of gas from gas source 24 into mixing chamber 20 through mixing chamber inlet 22. Mixing chamber 20 includes a first inlet port 19 and a second inlet port 21. A high pressure gas source 24 is coupled to the second inlet port 21 by mixing chamber inlet 22. Valve 60 can, for example, be a manually operated valve, a throttling valve, an automatic valve, or a computer controlled valve. In other embodiments (not shown), the gas entering mixing chamber inlet 22 can be drawn from ambient air.

A first end 23 of inlet tube 26 is coupled by a gas tight seal to first inlet port 19 of mixing chamber 20. A second end 27 of inlet tube 26 is adapted to receive an aerosol to be measured from aerosol generating device 30. Ambient air, or gas from another source (not shown) can also be received by inlet tube 26 through its second end 27.

During operation of aerosol measuring system 10, gas flow through measuring instrument 12 is set to a desired constant level by adjusting vacuum source 18. When vacuum source 18 is operating, gas will flow at a known rate through measuring instrument 12, for example, vacuum source 18 is preferably capable of generating a gas flow from about 15 to about 120 liters per minute. Gas flowing through the measuring instrument 12 as a result of the vacuum created by vacuum source 18 enters the gas regulating and aerosol conduit assembly 28 and thereafter measuring instrument 12, through the second end 27 of inlet tube 26 and through mixing chamber inlet 22.

Valve 60 will be adjusted to establish a desired flow of ambient air mixing chamber inlet 22. The remaining gas flow needed to make up the difference between that established by vacuum source 18 and that provided by mixing chamber inlet 22 is drawn through first inlet port 19 of mixing chamber 20. The flow into mixing chamber inlet 22 will typically be adjusted so that the flow rate through second end 27 of inlet tube 26 will be at the desired flow rate.

Specifically, the size distribution of an aerosol generated by a metered dose inhaler (MDI), i.e., aerosol generating device 30, can be measured using aerosol measuring system 10 shown in FIG. 1 as follows. The measuring instrument 12 is calibrated for the desired flow, e.g., 100 liters/minute (l/m). The vacuum source 18 connected to the measuring instrument 12 is turned on, and flow rate through the measuring instrument 12 adjusted to 100 l/m. A high pressure gas source 24 is connected to the mixing chamber inlet 22. The aerosol generating device 30 is attached to the inlet tube 26. The amount of gas traveling into the mixing chamber 20 is controlled by valve 60 connected to the high pressure gas source 24. If the aerosol is to be measured in a flow of 55 l/m through the inlet tube 26, the flow rate through the second inlet port 21 to the mixing chamber 20 is set at 45 l/m by adjusting the valve 60. In this manner, the gas flow rate through the inlet tube 26 is set to 55 l/m (100−45=55 l/m). The aerosol generating device 30 is then manually actuated and the aerosol travels through the inlet tube 26 at a rate of 55 l/m. The aerosol stream is then diluted by the additional gas stream introduced to the mixing chamber 20 by the mixing chamber inlet 22. Sizing inside the measuring instrument 12 thus takes place at a constant flow rate of 100 l/m.

Figure 2:
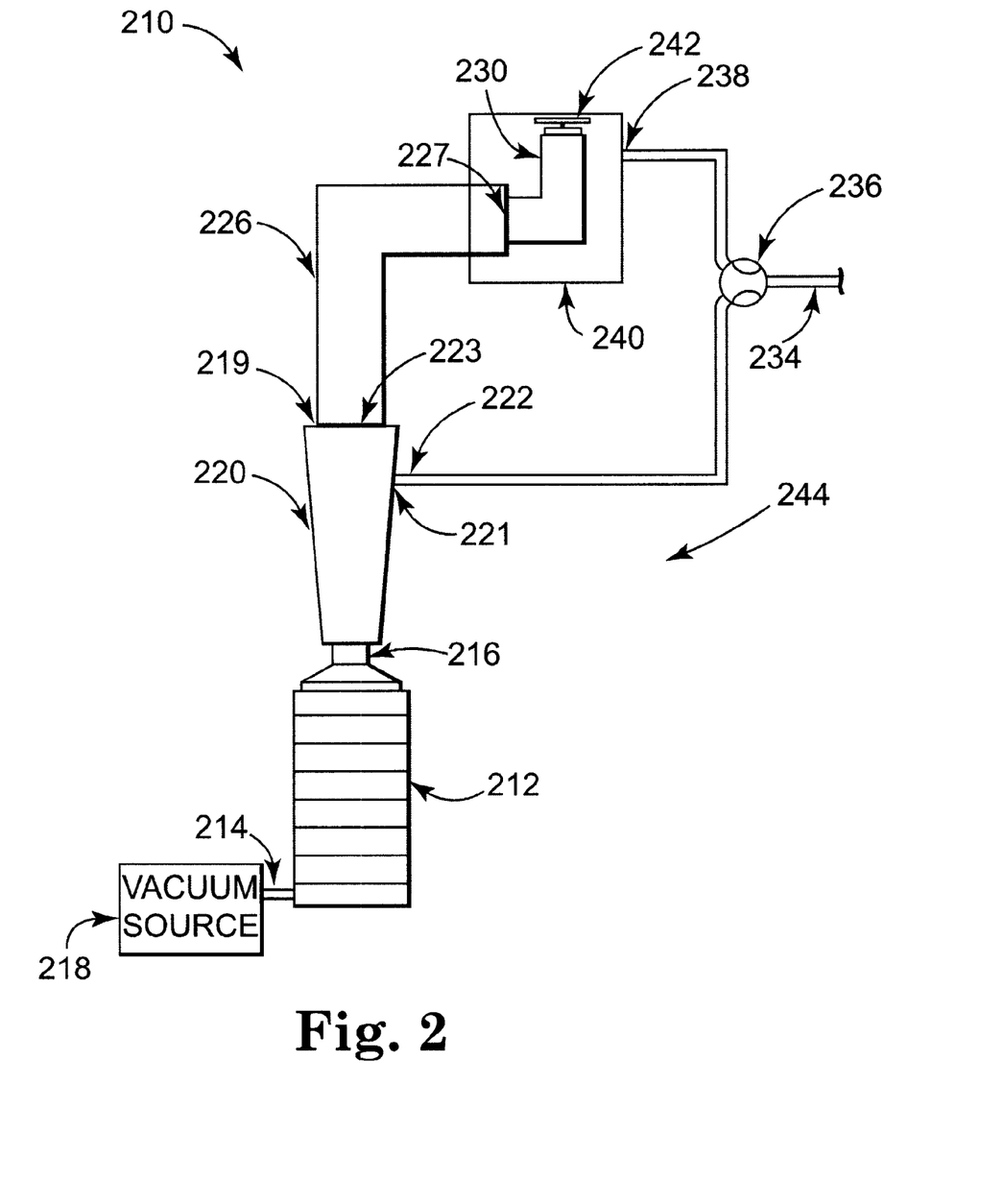
FIG. 2 is a schematic side view of a second embodiment of the improved apparatus in accordance with the present invention.

Referring now to FIG. 2, there is illustrated a schematic side view of a second embodiment of the invention, aerosol measuring system 210. Components which are functionally and/or structurally similar to those of system 10 are identified the same number incremented by 200. Aerosol measuring system 210 includes a measuring instrument 212 and a gas regulating and aerosol conduit assembly 244 for coupling an aerosol generating device 230 to the measuring instrument 212. Measuring instrument 212 can be a commercially available or otherwise conventional cascade impactor, and has a vacuum port 214 and an aerosol receiving inlet port 216. A vacuum source 218 is connected to vacuum port 214 to generate a flow of air or other gas into measuring instrument 212 through aerosol receiving inlet port 216. Typically, vacuum source 218 is adjusted to generate a gas flow of a predetermined rate into measuring instrument 212.

Gas regulating and aerosol conduit assembly 244 includes a mixing chamber 220, inlet tube 226, gas tight plenum 240 and proportioning valve 236. Proportioning valve 236 is positioned on conduit 234 and serves to bifurcate and proportion the flow of gas drawn from ambient air between mixing chamber inlet 222 and plenum inlet 238. Proportioning valve 236 can be a manually operated valve, a throttling valve, an automatic valve, or a computer controlled valve. Additionally, proportioning valve 236 can provide a constant or a time-varying flow.

Mixing chamber 220 includes a first inlet port 219 and a second inlet port 221. A first end 223 of inlet tube 226 is coupled by a gas tight seal to first inlet port 219 of mixing chamber 220. A second end 227 of inlet tube 226 opens into gas tight plenum 240 is adapted to receive an aerosol to be measured from aerosol generating device 230. Gas drawn from ambient air through conduit 234 into gas tight plenum 240 can also be received by inlet tube 226 through its second end 227.

Gas tight plenum 240 sealably surrounds the second end 227 of inlet tube 226. Gas tight plenum 240 may be made of machined metal or molded plastic or other suitable material. Conduit 234, left open to ambient air, is coupled to gas tight plenum 240 by plenum inlet 238.

Optionally, actuator 242 may be providing for activating aerosol generating device 230 so as to release an amount of aerosol into aerosol measuring system 210. Actuator 242 may be any mechanical, electrical, pneumatic, or other activation mode effective to generate an aerosol from aerosol generating device 230, providing that the activation mode chosen allows gas tight plenum 240 to remain gas tight.

During operation of aerosol measuring system 210, gas drawn from ambient air enters the system through conduit 234, at a value equal to and determined by the constant flow rate through measuring instrument 212, as generated by vacuum source 218. In operation, the gas flow entering aerosol measuring system 210 through conduit 234 is split by proportioning valve 236, so that the flow rate into gas tight plenum 240 through plenum inlet 238 matches the desired flow rate profile in which the aerosol is desired to be measured. The remaining gas entering aerosol measuring system 210 through conduit 234 is directed through mixing chamber inlet 222 to mixing chamber 220, so that the gas flow through measuring instrument 212 remains at a constant value.

Specifically, the size distribution of an aerosol generated by a metered dose inhaler (MDI), i.e., aerosol generating device 230, can be measured using aerosol measuring system 210 shown in FIG. 2 as follows. The measuring instrument 212 is calibrated for the desired flow, e.g., 100 l/m. The vacuum source 218 connected to the measuring instrument 212 is turned on, and flow rate through the measuring instrument 212 adjusted to 100 l/m. The amount of gas, drawn from ambient air, traveling into gas tight plenum 240 and into mixing chamber 220 is controlled by proportioning valve 236. If the aerosol is to be measured in a flow of 55 l/m through the inlet tube 226, the flow rate through the plenum inlet 238 is set at 55 l/m by adjusting the proportioning valve 236. The flow rate through mixing chamber inlet 222 will thus be 45 l/m (100 l/mn−55 l/m). The aerosol generating device 230 is inserted into gas tight plenum 240 and attached to the inlet tube 226, so that a leak-free seal exists between the gas tight plenum 240 and the second end 227 of inlet tube 226. The aerosol generating device 230 is actuated via actuator 242 and the generated aerosol travels through the inlet tube 226 at a rate of 55 l/m. The aerosol stream is then diluted by the additional gas stream introduced to the mixing chamber 220 by the mixing chamber inlet 222. Sizing inside the measuring instrument 212 thus takes place at a constant flow rate of 100 l/m.

Figure 3:
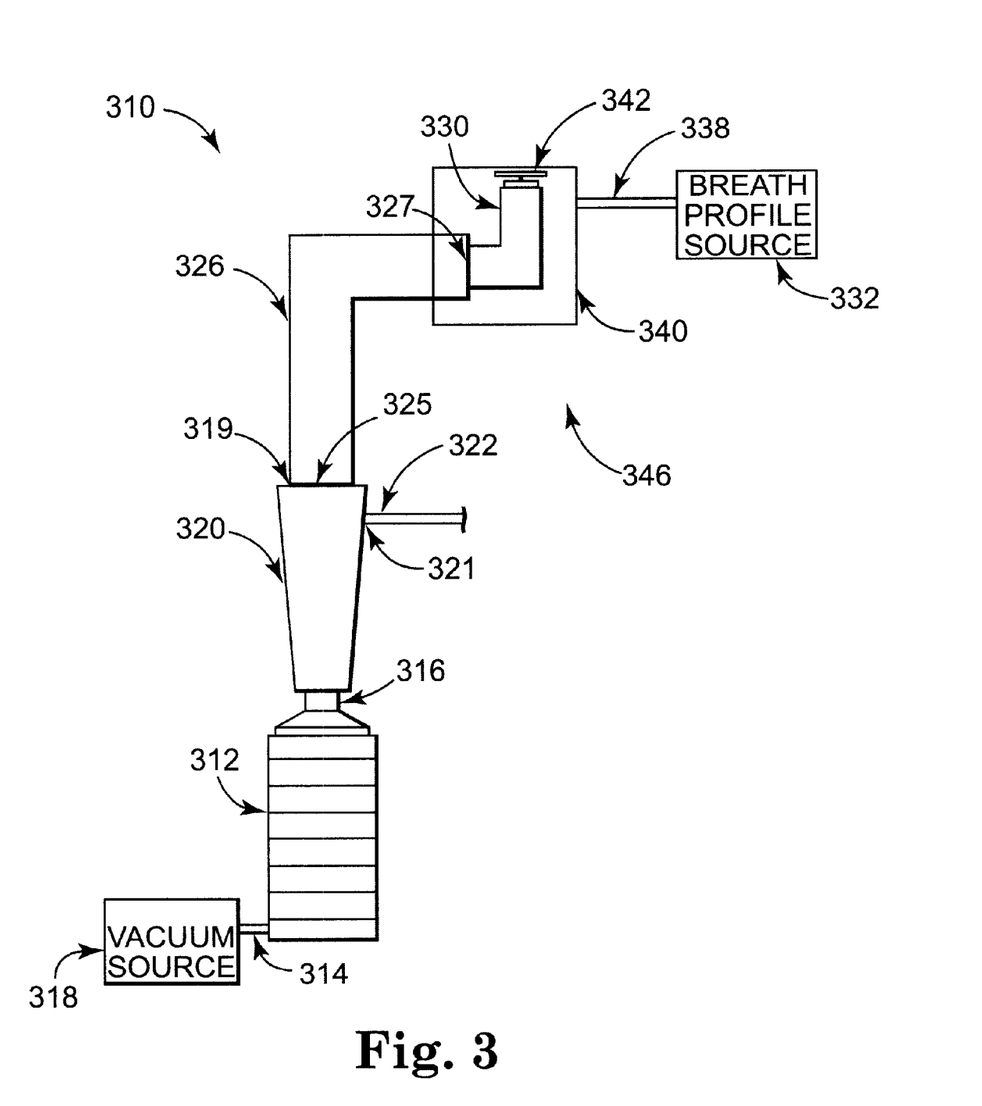
FIG. 3 is a schematic side view of a third embodiment of the improved apparatus in accordance with the present invention.

FIG. 3 is a schematic side view of a third embodiment of the invention, improved aerosol measuring system 310 in accordance with the present invention. Components which are functionally and/or structurally similar to those of system 10 are identified the same number incremented by 300. Aerosol measuring system 310 includes a measuring instrument 312 and a gas regulating and aerosol conduit assembly 346 for coupling an aerosol generating device 330 to the measuring instrument 312. Measuring instrument 312 can be a commercially available or otherwise conventional inertial classifier or other measurement device capable of measuring the size distribution of particles in an aerosol. Measuring instrument 312 has a vacuum port 314 and an aerosol receiving inlet port 316. A vacuum source 318 is connected to vacuum port 314 to generate a flow of air or other gas into measuring instrument 312 through aerosol receiving inlet port 316. Typically, vacuum source 318 is adjusted to generate a gas flow of a predetermined rate into measuring instrument 312.

Gas regulating and aerosol conduit assembly 346 includes a mixing chamber 320, inlet tube 326, a breath profile source 332 and gas tight plenum 340. Gas is drawn from ambient air and travels through mixing chamber inlet 322 into mixing chamber 320.

Mixing chamber 320 includes a first inlet port 319 and a second inlet port 321. A first end 323 of inlet tube 326 is coupled by a gas tight seal to first inlet port 319 of mixing chamber 320. A second end 327 of inlet tube 326 opens into gas tight plenum 340, and is adapted to receive an aerosol to be measured from aerosol generating device 330. Gas from breath profile source 332 can also be received by inlet tube 326 through its second end 327 after passing through aerosol generating device 330.

Gas tight plenum 340 sealably surrounds the second end 327 of inlet tube 326. Gas tight plenum 340 may be made of machined metal or molded plastic or other suitable material. Breath profile source 332 is coupled to gas tight plenum 340 by plenum inlet 338. Examples of commercially available breath profile source 332 suitable for use in the aerosol measuring system 310, and in the practice of the process of the present invention, are TSI model 8091 Breathing Simulator, commercially available from TSI Inc., St. Paul, Minn., the Aero-Breather™, commercially available from Amherst Process Instruments, Hadley, Mass. or the animal respirator, commercially available from Harvard Apparatus, Holliston, Mass. Alternatively, breath profile source 332 may simply be a bellows driven by a computer-controlled stepper motor.

Optionally, actuator 342 may be provided for activating aerosol generating device 330 so as to release an amount of aerosol into aerosol measuring system 310. Actuator 342 may be any mechanical, electrical, pneumatic, or other activation mode effective to generate an aerosol from aerosol generating device 330, provided that the chosen activation mode allows gas tight plenum 340 to remain gas tight.

During operation of aerosol measuring system 310, gas flow through measuring instrument 312 is set to a desired constant level by adjusting vacuum source 318. Gas flowing through the measuring instrument 312 as a result of the vacuum created by vacuum source 318 enters the gas regulating and aerosol conduit assembly 346 and thereafter measuring instrument 312, through the second end 327 of inlet tube 326 and through mixing chamber inlet 322.

Breath profile source 332 will be adjusted to provide the desired breath profile of time-varying flow rate through gas tight plenum 340, and thus, inlet tube 326 through second end 327. The flow into inlet tube 326 through second end 327 will typically be adjusted to a value equal to and representative of a breath flow rate at which the aerosol is desired to be tested. The remaining gas flow needed to make up the difference between that established by vacuum source 318 and that provided by inlet tube 326 is drawn through mixing chamber inlet 322. Mixing chamber inlet 322 may simply be left open to ambient air.

Specifically, the size distribution of an aerosol generated by a dry powder inhaler (DPI), i.e., aerosol generating device 330, can be measured using aerosol measuring system 310 shown in FIG. 3 as follows. The measuring instrument 312 is calibrated for the desired flow rate, e.g., 120 l/m. The aerosol generating device 330 is inserted into the gas tight plenum 340 and connected to the inlet tube 326, so that a leak-free seal exists between the gas tight plenum 340 and the second end 327 of inlet tube 326. Thus, air entering second end 327 of inlet tube 326 consists solely of air tat has passed through aerosol generating device 330. The plenum inlet 338 is attached to a breath profile source 332. The vacuum source 318 is turned on and the flow rate through the measuring instrument 312 adjusted to 120 l/m.

Initially, all the gas enters aerosol measuring system 310 through mixing chamber inlet 322, as drawn in by the vacuum source 318. A signal is given to initiate motion of the breath profile source 332 in such a fashion that the gas flow into the gas tight plenum 340 is flowing according to a time-changing profile which approximates the incoming air flow profile that a person generates during inhalation. This time-varying flow enters the gas tight plenum 340, causing an identical time-varying flow rate through the aerosol generating device 330. This flow automatically causes the aerosol generating device 330 to release an amount of aerosol. The aerosol then travels through the inlet tube 326 at the same time-varying flow rate. The gas entering the mixing chamber inlet 322 automatically decreases so that the flow rate through the measuring instrument 312 remains at a constant level of 120 l/m.

Figure 4:
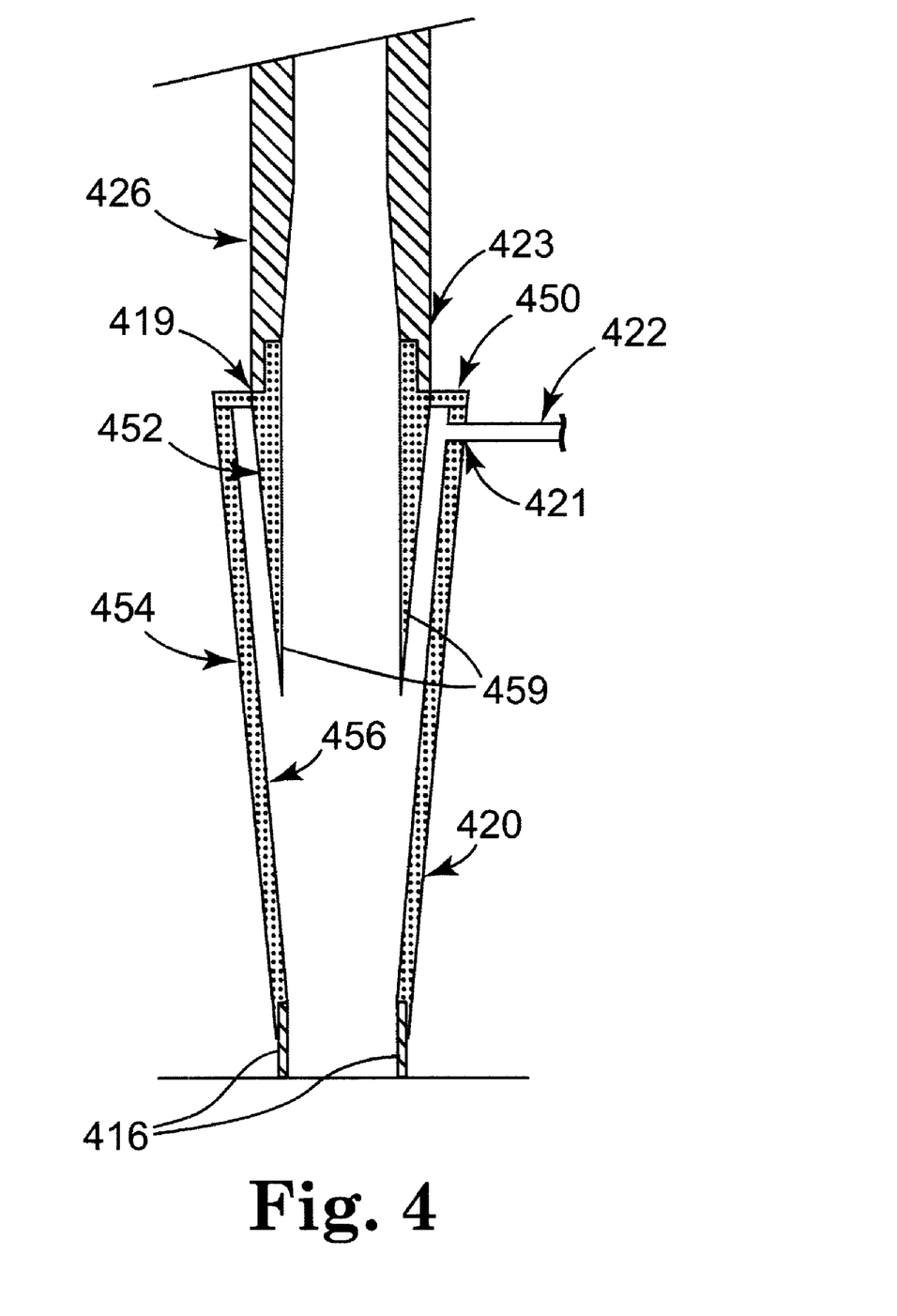
FIG. 4 is a detailed, cross-sectional view of the connection region between the inlet tube and the mixing chamber as may exist in the embodiments of the present invention illustrated in FIGS. 1, 2 and 3.

Referring now to FIG. 4, there is illustrated a detailed cross-sectional view of a preferred configuration of the connection region between inlet tube 426 and mixing chamber 420. Components which are functionally and/or structurally similar to those of system 10 are identified the same number incremented by 400. As is illustrated, mixing chamber 420 is sealably connected to measuring instrument (not shown in FIG. 4) by aerosol receiving inlet port 416. Inlet tube 426 is sealably connected to mixing chamber 420. Mixing chamber 420 comprises a substantially tubular body with external surface 454 and internal surface 456. Mixing chamber 420 further comprises an internal, substantially tubular member 459 with external surface 452. The internal diameter of inlet tube 426 is substantially the same as the internal diameter of the internal tubular member 459 of mixing chamber 420.

As is shown, external surface 454 of mixing chamber 420 is sealed by surface 450. Thus, gas may enter mixing chamber 420 through inlet tube 426 or mixing chamber inlet 422. By design, the gas that enters through mixing chamber inlet 422 is directed downward along external surface 452 of the internal tubular member 459 of mixing chamber 420. Thus, this gas is forced to travel through the channel created by external surface 452 of the internal tubular member 459 of mixing chamber 420 and internal surface 456 of mixing chamber 420, thereby becoming evenly distributed in an annular shape around the axis of the gas flow through inlet tube 426 before it reaches the end of internal tubular member 459. In this manner, the deposition of aerosol particles on the internal surface 456 of mixing chamber 420 may be minimized.

Figure 5:
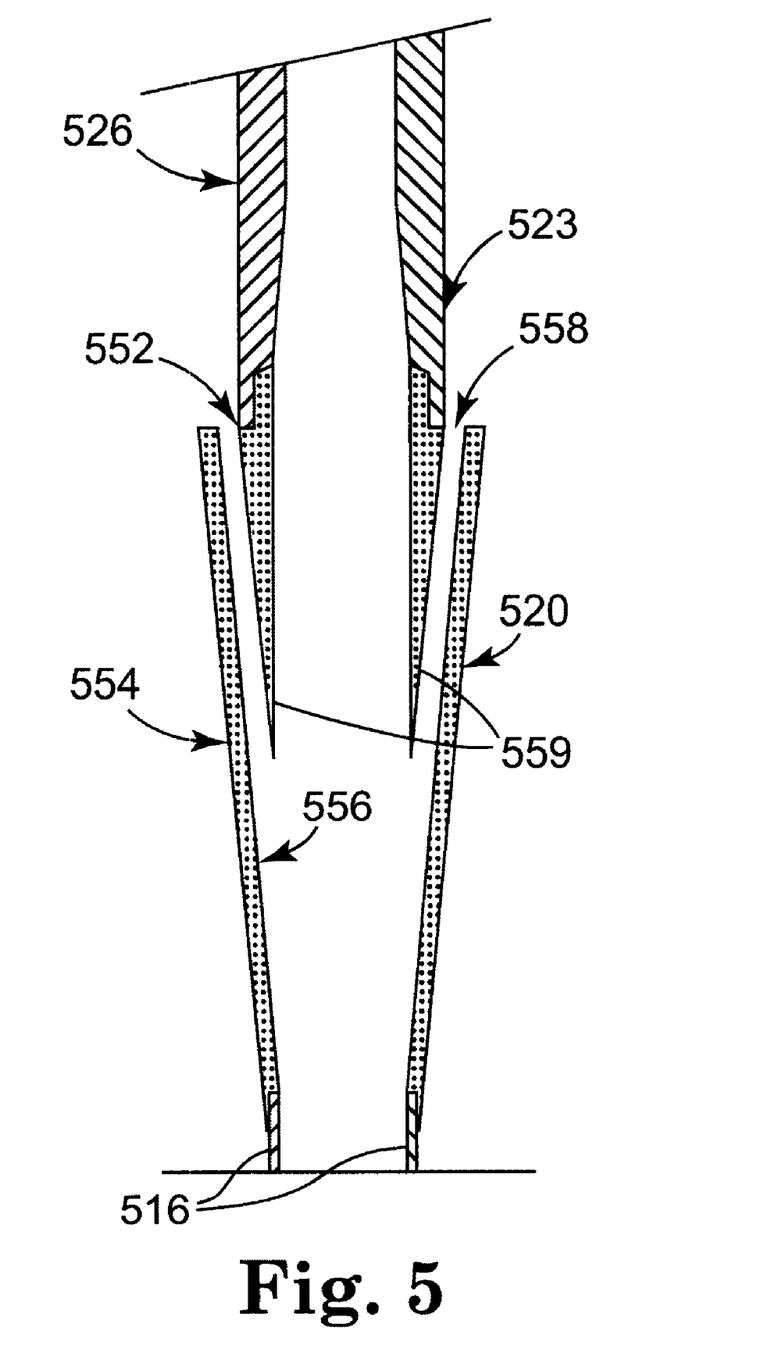
FIG. 5 is a detailed, cross-sectional view of the connection region between the inlet tube and the mixing chamber as it exists in a second embodiment of the improved apparatus of the present invention.

FIG. 5 is a detailed, cross-sectional view of a second embodiment of the connection region between inlet tube 526 and mixing chamber 520. Components which are functionally and/or structurally similar to those of system 10 are identified the same number incremented by 500. As is illustrated, mixing chamber 520 is sealably connected to the measuring instrument (not shown) by aerosol receiving inlet port 516. Mixing chamber 520 comprises a substantially tubular body with external surface 554 and internal surface 556. Mixing chamber 520 further comprises an internal, substantially tubular member 559 with external surface 552. The external surface 552 of the internal tubular member 559 and the internal surface 556 of mixing chamber 520 form gap 558, through which ambient air may enter mixing chamber 520. Thus, gas may enter mixing chamber 520 through inlet tube 526 or gap 558.

By design, the gas that is drawn through gap 558 as a result of the vacuum created by the vacuum source (not shown in FIG. 6) is directed downward along the external surface 552 of internal tubular member 559 of mixing chamber 520. Thus, this gas is forced to travel through the channel created by external surface 552 of internal tubular member 559 and internal surface 556 of mixing chamber 520, thereby becoming evenly distributed in an annular shape around the axis of the gas flow through inlet tube 526 before it reaches the end of internal tubular member 559. Thus, FIG. 5 illustrates another embodiment wherein the deposition of aerosol particles on the internal surface 556 of mixing chamber 520 is minimized.

Although the figures contain a single representation of the measuring instrument, the aerosol generating device and the inlet tube, the measuring system and process of the present invention may be practiced and/or utilize a wide range of types of aerosol generating devices, measuring instruments and inlet tubes. For example, the present invention provides an effective measuring system and process for measuring the particle size characteristics of aerosols generated by self-propelled aerosol delivery devices, such as metered dose inhalers, breath-propelled aerosol delivery devices, dry powder inhalers and the like. The aerosol generated by nebulizers can also be tested by the described measuring system and process.

Likewise, the measuring instrument can be any type of particle size measuring instrument generally requiring a constant rate of gas flow through the instrument provided that this flow rate is greater than or equal to the flow rate through the aerosol generating device. Finally, although the inlet tube shown is a commonly used inlet tube; the described measuring system and process can utilize any other inlet tube capable of effectively coupling the aerosol generating device to the measuring instrument.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. An improved apparatus for the measurement of the size of aerosolized particles of pharmaceutical compounds of the type intended for oral delivery to a patient, comprising:
   an instrument for measuring the size of aerosolized particles, said instrument being of the type utilizing a generally constant instrument gas flow rate;
   a first inlet coupled to the instrument for receiving a first gas flow at a predetermined test rate that is less than the instrument gas flow rate, the first gas flow including a carrier gas flow and aerosolized particles of pharmaceutical compounds to be measured that are introduced into the carrier gas flow;
   a second inlet coupled to the instrument for receiving a second gas flow that is free of aerosolized particles of pharmaceutical compounds to be measured; and
   a flow adjusting mechanism for causing the sum of the first gas flow and the second gas flow to equal the constant instrument gas flow rate while maintaining the first gas flow at the predetermined rate.

2. The improved apparatus of claim 1 wherein the predetermined test rate is a constant rate.

3. The improved measuring system of claim 1 wherein the predetermined test rate is a varying rate.

4. An improved measuring system for the measurement of the size of aerosolized particles of pharmaceutical compounds of the type intended for oral delivery to a patient, comprising:
   a measuring instrument for measuring the size of aerosolized particles, said instrument being of the type utilizing a generally constant instrument gas flow rate;
   an aerosol conduit assembly for coupling an aerosol generating device to the measuring instrument and for receiving a first gas flow at a predetermined test rate that is less than the instrument gas flow rate, the first gas flow including a carrier gas flow and aerosolized particles of pharmaceutical compounds to be measured that are introduced into the carrier gas flow by an aerosol generating device; and
   a gas regulating conduit assembly for receiving a second gas flow that is free of aerosolized particles of pharmaceutical compounds to be measured and for coupling the aerosol conduit assembly to the measuring instrument;
   wherein the instrument gas flow through the measuring instrument is maintained by causing the sum of the first gas flow and the second gas flow to equal the constant instrument gas flow rate while maintaining the first gas flow at the predetermined test rate.

5. The improved measuring system of claim 4, wherein the aerosol conduit assembly comprises an inlet tube comprising a first end and a second end, wherein the second end of the inlet tube is adapted to receive aerosolized particles from an aerosol generating device.

6. The improved measuring system of claim 5, wherein the gas regulating conduit assembly comprises:
   a mixing chamber comprising a first inlet port and a second inlet port;
   an inlet coupled to a gas source; and
   a valve,
      wherein said valve is positioned on the inlet and is actuated to regulate the flow of gas from the gas source into the mixing chamber through the inlet.

7. The improved measuring system of claim 6, wherein the first end of the inlet tube is coupled to the first inlet port of the mixing chamber.

8. The improved measuring system of claim 7, wherein the second end of the inlet tube is adapted to receive an additional amount of gas.

9. The improved measuring system of claim 8, wherein the additional amount of gas is ambient air.

10. The improved measuring system of claim 8, wherein the gas comprises gas produced by a breath profile source.

11. The improved measuring system of claim 10, wherein a gas tight plenum sealably surrounds the second end of the inlet tube.

12. The improved measuring system of claim 6, wherein the aerosol conduit assembly further comprises:
   a gas tight plenum comprising a plenum inlet;
   a breath profile source; and
   a conduit coupling the gas tight plenum to the breath profile source.

13. The improved measuring system of claim 12, wherein the first end of the inlet tube is coupled to the first inlet port of the mixing chamber.

14. The improved measuring system of claim 13, wherein the second end of the inlet tube is adapted to receive an additional amount of gas.

15. The improved measuring system of claim 5, wherein the gas regulating conduit assembly further comprises:
   a mixing chamber comprising a first inlet port and a second inlet port; and
   a mixing chamber inlet coupled to a gas source.

16. The improved measuring system of claim 15, wherein the gas source is ambient air.

17. The improved measuring system of claim 16, wherein the aerosol conduit assembly further comprises:
   a gas tight plenum comprising a plenum inlet;
   a conduit coupling the gas tight plenum to a breath profile source; and
   a proportioning valve,
      wherein the proportioning valve is positioned on the conduit and serves to bifurcate and proportion the flow of gas drawn from ambient air between the mixing chamber inlet and the plenum inlet.

18. The improved measuring system of claim 17, wherein the first end of the inlet tube is coupled to the first inlet port of the mixing chamber.

19. The improved measuring system of claim 7, 18 or 13, wherein:
 the mixing chamber comprises a substantially tubular body with an internal and an external surface and an internal, substantially tubular member; and
 the inlet tube comprises a substantially tubular body of substantially the same diameter as the internal tubular member of the mixing chamber.

20. The improved measuring system of claim 19, wherein the external surface of the mixing chamber is sealably coupled to the inlet tube.

21. The improved measuring system of claim 19, wherein the external surface of the internal tubular member of the mixing chamber and the internal surface of the mixing chamber form a gap through which a gas may flow.

22. The improved measuring system of claim 18, wherein the second end of the inlet tube is adapted to receive an additional amount of gas.

23. The improved measuring system of claim 22, wherein the additional amount of gas comprises gas drawn from ambient air.

24. The improved measuring system of claim 23, wherein the gas tight plenum sealably surrounds the second end of the inlet tube.

25. The improved measuring system of claim 4 wherein the predetermined test rate is a constant rate.

26. The improved measuring system of claim 4 wherein the predetermined test rate is a varying rate.

* * * * *